United States Patent [19]
Knoth

[11] 3,945,249
[45] Mar. 23, 1976

[54] TESTING APPARATUS FOR STRUCTURAL MEMBERS

[75] Inventor: Wayne Knoth, Granger, Ind.

[73] Assignee: Universal Forest Products, Inc., Grand Rapids, Mich.

[22] Filed: July 1, 1974

[21] Appl. No.: 484,854

[52] U.S. Cl. .................................................. 73/94
[51] Int. Cl.² ........................................... G01N 3/08
[58] Field of Search ....... 73/88 R, 89, 90, 100, 103, 73/94

[56] References Cited
UNITED STATES PATENTS

| | | | |
|---|---|---|---|
| 2,058,444 | 10/1936 | Harrison | 73/88 R |
| 2,151,584 | 3/1939 | Bagatti | 73/88 R |
| 2,668,444 | 2/1954 | Berman | 73/88 R |
| 3,313,147 | 4/1967 | Rebbeck | 73/88 R |
| 3,512,404 | 5/1970 | Jureit | 73/100 X |
| 3,714,820 | 2/1973 | Strickler et al. | 73/89 |
| 3,871,213 | 3/1975 | Jureit et al. | 73/94 |

*Primary Examiner*—Jerry W. Myracle
*Attorney, Agent, or Firm*—McGarry & Waters

[57] ABSTRACT

Testing apparatus for measuring the load bearing capabilities of structural members under a uniform load comprises a fixed base that supports one side of the structural member; a flexible, inflatable tube engaging the length of a second side of the structural member opposite the first side; a restraining mechanism extending along the length of the tube and adapted to urge the tube against the second side of the structural member as the tube is inflated; a suitable air pressure source for inflating the tube; and a load sensing device for measuring the load placed on the structural member by the inflation of the tube. The restraining mechanism comprises a plurality of channel sections arranged end to end and positioned over the inflatable tube a predetermined distance from the second side of the structural member. The channel sections are mounted on brackets that are in turn slidably mounted on parallel guide rails that run transversely to the structural member. Fasteners are provided in the mounting brackets so that the channels can be fixed in any position at any point along the guide rails, thereby permitting the channel sections to be relocated to conform with the outer contour of structural members having a variety of different shapes.

15 Claims, 4 Drawing Figures

TESTING APPARATUS FOR STRUCTURAL MEMBERS

BACKGROUND OF THE INVENTION

1. Field of the Invention

This invention relates to load testing apparatus for testing the ability of a structural member to withstand uniform loads placed along the length of the structural member.

2. Description of the Prior Art

Prefabricated structural members are used in a number of industries, one of which is the mobile home industry. The roof of a mobile home is supported by any one of a variety of types of rafter or truss structures, depending upon the shape of the roof. Such structures include monopitch, bow truss, and A-type rafters.

It is necessary that such rafter structures be able to support a fairly substantial load placed on the roof of a mobile home. Accordingly, the load bearing capabilities of prefabricated structural members are tested on a regular basis. The test generally employed on prefabricated rafter or truss structures is to place each end of the rafter on a support and load the middle portion of the rafter at a series of points along the rafter with cement blocks or the like until the rafter breaks under the load. The amount of weight placed on the rafter and the spacing of the weights is predetermined by code, and the rafter must be able to support this load in order to be satisfactory. The applicable code specifies that the rafter be loaded with weights such as cement blocks or other suitable loading device such that any concentrated loads are one foot apart or less. An alternative to cement blocks in a series of point loads applied by individual hydraulic cylinders spaced along the truss or rafter.

The principal problem with the types of rafter testers used previously is that they test the rafter under unrealistic conditions by placing separate loads along the rafter structure. When a rafter structure is covered by the roof of a mobile home, the load placed on the rafter structure by snow or the like is uniformly distributed over the length of the rafter, and the stress generated by such a uniform load could be entirely different from the nature of the stress exerted at a series of individual positions along the rafter structure. Thus, such testers are inaccurate in determining the overall strength or weakness of the rafter structure.

SUMMARY OF THE INVENTION

In accordance with the present invention, testing apparatus for measuring the load bearing capabilities of a structural member under a uniform load comprises a fixed base adapted to support one side of the member and a pressure applying mechanism adapted to apply a uniform pressure along a second side of the structural member opposite the first side. A load sensing device is employed to measure the load placed on the structural member by the pressure applying mechanism. The pressure applying mechanism comprises a flexible, inflatable tube engaging substantially the entire length of the second side of the structural member and a restraining mechanism positioned adjacent the outside surface of the tube, which has a contour that substantially conforms with the outer contour of the second side of the structural member. The restraining mechanism restrains the outward expansion of the tube away from the second side of the structural member upon inflation of the tube so as to urge expansion of the tube uniformly against the second side of the member. The contour of the restraining mechanism is changeable so that the restraining mechanism can be made to substantially conform with the outer contour of structural members having different shapes. An air pressure source is employed for inflating the tube so as to produce a predetermined load on the member.

An important feature of the present invention is that the restraining mechanism is formed of a series of segmented channel sections arranged end to end adjacent the second side of the structural member. Each channel section extends downwardly over the tube and is positioned a predetermined distance away from the second side of the structural member. Each channel section is mounted on a bracket, and each bracket is slidably mounted on a guide rail that extends transversely to the longitudinal direction of the structural member. Suitable fastening devices are provided for each mounting bracket for fixing the bracket in any predetermined position along the guide rail. With this type of restraining mechanism, the restraining mechanism can be employed for measuring the load bearing capabilities of many different shapes of rafters, including monopitch, bow truss, and A-type rafters, as well as for testing floor beams and measuring the modulus of rupture and the deflection of other studs and beams.

Another important feature of the present invention is that the flexible, inflatable tube employed in connection with this invention is of the type that expands resiliently upon the continued inflation of the tube. The resilient expandability of the tube is important in order to maintain a uniform load on the structural member even after the member has deflected somewhat under the stress placed on it by the inflation of the tube. In a straight structural member, such as a beam or the like, for example, if the beam is supported on the base only at each end thereof, placing a uniform load along the top side of the beam will cause the beam to bow downwardly at the center. If the tube were not continuously expandable upon inflation, the tube would reach a maximum outer diameter at the center of the beam and after that point it would not continue to exert additional pressure on the beam. Thus, as the pressure within the tube continued to be increased, the pressure of the tube on the beam would become greater at the ends of the beam than at the center of the beam. This is an unrealistic situation that should be avoided in testing apparatus.

In accordance with the present invention, the type of tube used in connection with the rafter tester is the type of tube that might be used as a bicycle inner tube or the like. Such a tube will continue to expand until the tube bursts. A tube that would not be satisfactory in the present invention is a tube including nonexpandable, fibrous material that prevents the diameter of the tube from expanding past a certain point.

The testing apparatus of the present invention overcomes the deficiencies in prior methods for testing rafters and other types of structural members. The test need not be destructive of the rafter structure unless desired for specific testing purposes, and the test is easy to accomplish, thus saving testing time. Also, the load is placed uniformly along the entire length of the rafter, which is the same type of load that is placed on the rafter under actual operating conditions. This permits a much more realistic means for measuring the load bearing capabilities of the rafter under actual operating conditions.

Another advantage of the present invention is that by using segmented channel sections slidably mounted along guide rails, the rafter tester can be adapted to test many different shapes of rafters and structural members, while still retaining the desirable feature of placing a uniform load along the entire length of the structural member.

These and other features and advantages of the present invention will hereinafter appear, and for purposes of illustration, but not of limitation, a preferred embodiment of the present invention is shown and described in detail below and in the appended drawings.

DETAILED DESCRIPTION OF THE PREFERRED EMBODIMENT

Figure 1:
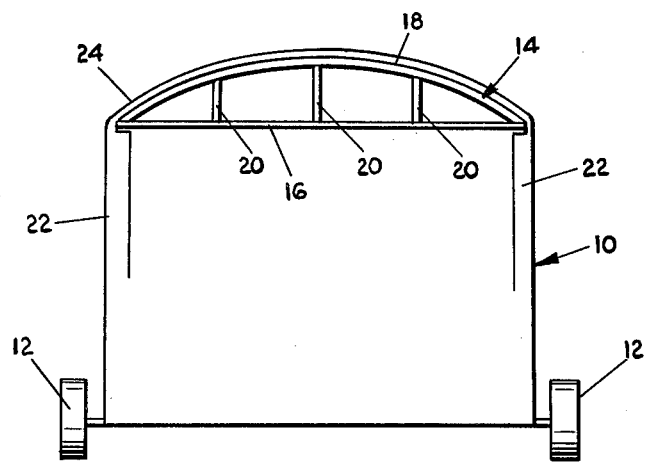
FIG. 1 is a pictorial view showing the manner in which a rafter or truss structure is incorporated in the structure of a mobile home.

Referring now to the drawings, a mobile home 10 having wheels 12 is shown in FIG. 1 incorporating a bow-shaped rafter structure 14 in the manner that it might be incorporated in actual operating conditions. Other shapes of rafters or trusses are used in mobile homes and all can be tested with the testing apparatus of the present invention. A single type of rafter structure is shown for exemplary purposes.

Rafter 14 includes a flat base or first side 16 and a curved top or second side 18 on the opposite side of the rafter structure. Cross braces 20 are provided in order to maintain the rigidity of the structure. Base 16 is supported in the mobile home by means of suitable structural members 22 in the sides of the mobile home. Thus, the rafter structure is supported in the mobile home only at the ends of the structure. The load on the rafter structure, on the other hand, is borne uniformly over the top 24 of the mobile home. Such a load could be generated by an accumulation of snow or other material on the top of the mobile home.

Figure 2:
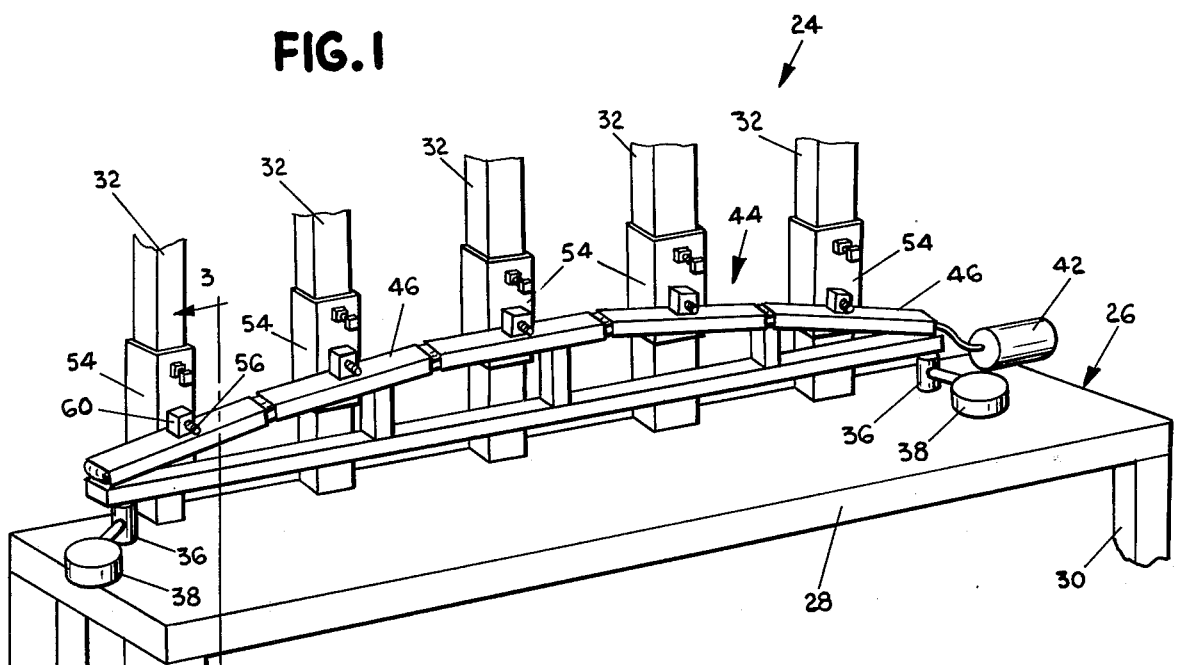
FIG. 2 is a pictorial view showing the testing apparatus of the present invention in the process of testing the load bearing abilities of a bow-shaped truss or rafter structure.
Figure 3:
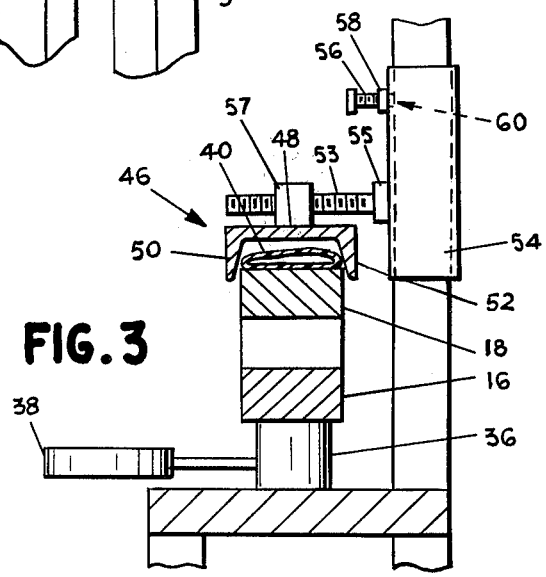
FIG. 3 is a view taken along line 3—3 of FIG. 2, showing the inflatable tube in a deflated condition.

In order to test the load bearing capabilities of rafter 14 under realistic conditions, testing apparatus 24 of the present invention is employed in the manner shown in FIG. 2. Testing apparatus 24 includes a base 26 having a flat top 28 and legs 30. The base may be formed so as to stand upright on its own or it may be mounted against a wall. Vertical guide rails 32 extend upwardly from the base in a direction transverse to the longitudinal direction of rafter 14. Guide rails 32 are attached to the base. They also can be rigidly fastened to a wall to provide additional support. Guide rails 32 preferably are formed of rectangular tubular members formed of steel or the like. In the preferred practice of the present invention, the top of the testing apparatus is about 14 feet long and 14 guide rails are spaced a foot apart along the length of the top. For illustrative purposes, only five guide rails are shown in the drawings.

Rafter 14 is mounted in the testing apparatus by resting the rafter on its bottom edge on top 28 of the base. The ends of base 16 are placed on load cells 36 (i.e., scales) at each end of the base, such that the rafter is supported on its ends, which is the same manner in which the rafter would be supported when incorporated in the structure of a mobile home. Load cells 36 include gauges 38 which extend outwardly from the testing apparatus so as to be easily viewable by an operator of the testing apparatus.

A flexible, inflatable tube 40, such as bicycle inner tube, is laid along the entire length of the curved top or second side 18 of the rafter structure. The inflatable tube 40 is connected to an air pressure source 42 such as a source of pressurized air or an air pump or the like. Air pressure source 42 is manually operable to inflate the tube.

In order to prevent the tube from expanding outwardly away from the second side of the rafter, thereby exerting no force on the rafter, a restraining mechanism 44 is mounted adjacent the outer surface of the tube. Restraining mechanism 44 extends along the length of the tube and prevents the tube from expanding outwardly when it is inflated. This restraining action urges the expansion of the tube downwardly against the top of the rafter being tested.

Restraining mechanism 44 comprises a series of restraining sections 46 in the form of inverted channels. The restraining sections or channels 46 are positioned end to end along the entire length of the tube and are each spaced a predetermined distance away from the second side of the rafter structure. Thus, when the tube is inflated, uniform pressure is exerted downwardly by the tube against the top or second side of the rafter structure.

Figure 4:
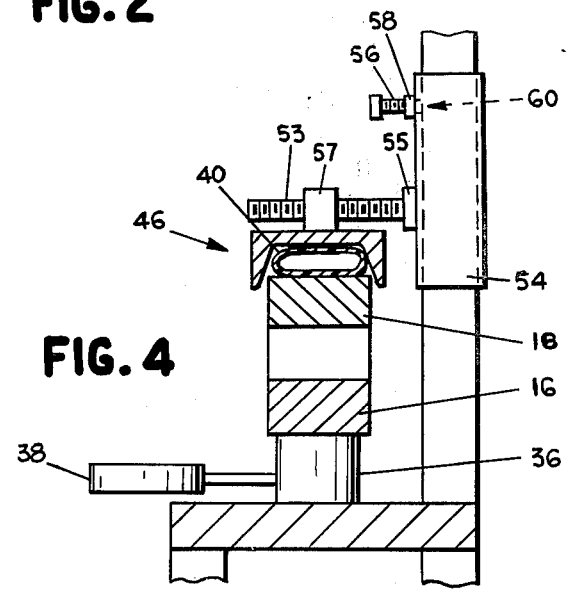
FIG. 4 is the same view as FIG. 3, showing the tube in an inflated condition.

Each channel section 46 comprises a base 48 that is generally parallel to the section of the rafter adjacent to it and outer and inner side flanges 50 and 52 respectively extending downwardly from base 48 over tube 40. The interior portion of the channel member thus forms a cavity that restricts the expansion of the tube 40 in an outward direction when it is inflated in the manner shown in FIG. 4.

Each channel section is mounted for vertical movement along its respective guide rail by means of a mounting bracket 54 that slides along the guide rails. Each mounting bracket is a tubular member of rectangular cross-section that fits closely over the rectangular guide rail.

Each channel section 46 is mounted on its mounting bracket 54 by means of a bolt or threaded rod 53 that extends outwardly from a head 55 which is attached to the outer surface of the mounting bracket. The channel section is pivotably mounted on bolt 53 by means of a mounting block 57 mounted on the top of the channel section. A threaded opening in block 57 engages bolt 53. Each channel section can be locked by any desired position on its guide rail by means of a locking bolt 56 that engages a nut 58 mounted on the mounting bracket and extends through an opening 60 in the mounting bracket into engagement with guide rail 32. The channel section can be moved to different positions and locked in place by simply loosening an tightening locking bolt 56.

The operation of the testing apparatus of the present invention should be self-evident from the foregoing description of the structure, but for purposes of clarity, a brief summary of this operation is as follows: After a rafter has been manufactured, it is inserted in rafter tester 24 with channel section 54 being maintained in a raised position. The tube is then laid along the top of the rafter structure and the channel members are moved downwardly and locked in a position a predetermined distance above the upper surface of the rafter structure. In order to avoid the necessity of repositioning the channel members with each test conducted, it also is possible to leave the channel members in position on the guide rail and lower the base by a suitable lowering device (now shown), in order to insert the rafter in the rafter tester.

After the rafter has been inserted in the testing apparatus, air pressure is introduced into the tube until the load cells mounted under the ends of the rafter structure reach a level sufficient to indicate that the structure has adequate load bearing capabilities. The air is then released from the tube and the rafter is removed from the testing apparatus.

Another use of this testing apparatus is to measure the deflection or modulus of rupture of studs and beams. For this purpose, suitable deflection measuring apparatus (not shown) is employed at appropriate points along the beam or stud being tested, in order to measure the deflection of the beam when subjected to the uniform load created by the inflatable tube.

It should be understood that the foregoing represents merely a preferred embodiment of the present invention and that various changes and modifications may be made in the arrangments and details of construction of the embodiment shown herein without departing from the spirit and scope of the present invention.

The embodiments of the invention in which an exclusive property or privilege is claimed are defined as follows:

1. Testing apparatus for measuring the load bearing capabilities of a structural member comprising:
    fixed base means adapted to support one side of the structural member;
    flexible, inflatable tube means adapted to engage substantially the entire length of a second side of a structural member, said second side being opposite the first side;
    restraining means positioned adjacent the outer surface of the tube means and having a contour that substantially conforms to the outer contour of the second side of the structural member, said restraining means being adapted to restrain the outward expansion of the tube means away from said second side upon inflation of the tube means so as to urge the expansion of the tube means uniformly against the second side of the structural member;
    air pressure means for inflating the tube means; and
    sensor means for measuring the load exerted on the member by the inflation of the tube means.

2. Testing apparatus as claimed in claim 1 wherein the contour of said restraining means is changeable such that the contour can be made to substantially conform with the outer contour of structural members having different shapes.

3. Testing apparatus as claimed in claim 2 wherein the restraining means comprises:
    a plurality of restraining sections arranged end to end along the length of the tube, each section being positioned a predetermined distance away from the outer surface of the second side of the structural member;
    a plurality of guide rails, one positioned adjacent each restraining section, extending in a transverse direction relative to the longitudinal direction of the structural member;
    a mounting bracket attached to each restraining section and slidably mounted for longitudinal movement on the guide rail adjacent said restraining section; and
    fastening means associated with each mounting bracket adapted to lock the mounting bracket in any desired position on the guide rail, whereby the positions of the restraining sections can be adjusted to conform with the outer contour of structural members having different shapes.

4. Testing apparatus as claimed in claim 3 wherein the restraining sections are channel sections that fit over the tube means.

5. Testing apparatus as claimed in claim 1 wherein:
    the first side of the structural member is supported by load cells mounted on the base at each end of the structural member, each load cell providing a separate reading of the force exerted on that particular load cell.

6. Testing apparatus as claimed in claim 1 wherein the tube means are adapted to continue to exert a substantially uniform pressure on the second side of the beam even though the contour of the second side changes as a result of deflection of the structural member caused by pressure exerted by the tube means.

7. Testing apparatus as claimed in claim 6 wherein the tube means is an elongated tube having substantially uniform cross sectional area prior to expansion of the tube, said tube being continuously expandable upon inflation of the tube such that a section of the tube adjacent a deflected portion of the rafter can expand more than another section of the tube adjacent an undeflected portion of the rafter, whereby a continuous uniform pressure may be applied to the rafter, even though the contour of the rafter changes as a result of rafter deflection.

8. Testing apparatus for measuring the load bearing capabilities of rafter structure for supporting a roof comprising:
    load cell means mounted in a fixed position and adapted to support the bottom of the rafter at predetermined points thereon and measure the load on the rafter at each such point; and
    fluid pressure applying means for applying a uniform downward pressure along the entire length of the top of the rafter.

9. Testing appparatus as claimed in claim 8 wherein the load cell means comprise individual load cells that support the rafter at each end thereof.

10. Testing apparatus as claimed in claim 8 wherein the pressure applying means is adapted to continue to apply a uniform pressure on the top of the rafter structure even if the contour of the rafter structure changes due to deflection of the structure resulting from the pressure applied thereto by the pressure applying means.

11. Testing apparatus as claimed in claim 10 wherein the pressure applying means comprises:
    a flexible, inflatable tube engaging the length of the top surface of the rafter, the walls of said tube being continuously expandable on inflation of the tube;
    air pressure means for inflating the tube to a predetermined pressure; and restraining means positioned over the tube and adapted to urge the expansion of the tube uniformly against the top of the beam upon inflation of the tube.

12. Testing apparatus as claimed in claim 11 wherein the restraining means extends substantially the length of the top of the rafter, said restraining means having a surface facing the top of the beam that conforms substantially with the contour of the top of the rafter and is positioned a predetermined distance therefrom, the contour of said surface being changable to conform with the contour of the top of a rafter having a different shape.

13. Testing apparatus as claimed in claim 12 wherein the restraining means comprises:
   a plurality of restraining sections positioned end to end along the length of the rafter; and
   mounting means for fixing each individual restraining section in a predetermined transverse position relative to the rafter structure.

14. Testing apparatus as claimed in claim 13 wherein the mounting means comprises:
   a fixed guide rail adjacent each restraining section extending transversely to the rafter;
   mounting bracket means attached to each restraining section and adapted to guide the restraining section in a longitudinal path along its respective guide rail; and
   fastener means attached to each mounting bracket for fixing each restraining section in any selected position along its respective guide rail.

15. Testing apparatus as claimed in claim 14 wherein:
   the guide rails are vertically disposed;
   the mounting bracket means comprise tubular members that fit closely over the guide rail so as to be slidable along the guide rails, said tubular members having horizontal rods extending outwardly therefrom over the tops of their respective restraining sections;
   the restraining sections are channel sections that fit over the tube, said channel sections comprising means on the top of the channel sections for pivotably mounting the channel sections on the rods extending from the tubular members; and
   the fastener means comprise bolts that are received in threaded openings through the tubular members, said bolts being axially movable by rotating the bolts such that the bolts engage the guide rails and lock their respective channel sections in desired positions on their guide rails.

* * * * *